(12) United States Patent
Warren et al.

(10) Patent No.: US 7,323,602 B2
(45) Date of Patent: Jan. 29, 2008

(54) PREPARATION PROCESS OF SOME HALOGENO-SUBSTITUTED MONOSULFIDES AND THEIR HYDROXY-MONOSULFIDE OR ISOTHIOURONIUM BROMIDE EQUIVALENTS AS INTERMEDIATES

(75) Inventors: Kenneth Edwin Herbert Warren, Cheshire (GB); Anne Margaret Lamont Kane, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 204 days.

(21) Appl. No.: 10/491,738

(22) PCT Filed: Oct. 3, 2002

(86) PCT No.: PCT/GB02/04478

§ 371 (c)(1),
(2), (4) Date: Aug. 30, 2004

(87) PCT Pub. No.: WO03/031399

PCT Pub. Date: Apr. 17, 2003

(65) Prior Publication Data

US 2005/0033085 A1 Feb. 10, 2005

(30) Foreign Application Priority Data

Oct. 5, 2001 (GB) .................................. 0123961.5

(51) Int. Cl.
*C07C 319/02* (2006.01)
*C07C 319/12* (2006.01)
*C07C 321/04* (2006.01)
*C07C 323/44* (2006.01)
*C07C 335/32* (2006.01)
*C07C 249/00* (2006.01)

(52) U.S. Cl. ............................ 568/56; 568/65; 564/17; 564/30; 564/248

(58) Field of Classification Search ...................... None
See application file for complete search history.

(56) References Cited

U.S. PATENT DOCUMENTS

| 4,659,516 A | 4/1987 | Bowler et al. |
| 5,502,046 A | 3/1996 | Bohlmann et al. |
| 5,552,391 A | 9/1996 | Coutts et al. |

FOREIGN PATENT DOCUMENTS

| EP | 0 322 390 | 6/1989 |
| WO | WO-93/06124 | 4/1993 |
| WO | WO-02/32922 | 4/2002 |

OTHER PUBLICATIONS

Database CASREACT on STN, No. 112:119207, Khimiya Prirodnykh Soedinenii (1989), 2, p. 232-6 (abstract).*

Database CASREACT on STN, No. 125:33418, Tetrahedron (1996), 52(16), p. 5989-98 (abstract).*
Database CASREACT on STN, No. 127:135439, J. of the American Chemical Society (1997), 119(28), p. 6674-6675 (abstract).*
Database CASREACT on STN, No. 110:230851, Gazzetta Chimica Italiana (1988), 118(9), p. 613-16 (abstract).*
Database CASREACT on STN, No. 50:35917, Acta Chemica Scandinavica (1955), 9, p. 721-6 (abstract).*
Datacase CASREACT on STN, No. 98:34449, J. of Organic Chemistry (1983), 48(1), p. 8-16 (abstract).*
Database CAPLUS of STN, Acc. No. 1988:111491, Phosphorus and Sulfur and the Related Elements (1987), 31(1-2), p. 161-75 (abstract).*
Database CAPLUS on STN, Acc. No. 1945:16001, J. of the American Society (1945), 67, p. 594-7 (abstract).*
Database CAPLUS on STN, Acc. No. 1966:77885, Experimental Parasitology (1965), 17(3), p. 302-8 (abstract).*
Database CAPLUS on STN, Acc. No. 1998:268835, Helvetica Chimica Acta (1998), 81(4), p. 646-660 (abstract).*
Database CAPLUS on STN, Acc. No. 1967:42328, FR 1443441 (Jun. 24, 1966) (abstract).*
Database CAPLUS on STN, Acc. No.1999:811229, WO 9965893 (Dec. 23, 1999) (abstract).*
Wakeling, A.E., "Therapeutic Potential of Pure Antioestrogens in the Treatment of Breast Cancer," J. Steroid Biochem. Molec. Biol., 37(6), 771-775 (1990).
Wakeling, A.E., et al., Steroidal Pure Antioestrogens, J. Endocr., 112, R7-R10 (1987).

(Continued)

*Primary Examiner*—Brian Davis

(57) ABSTRACT

A process for preparing an intermediate compound of formula (II)

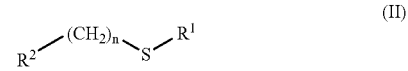

where n is an integer of from 3 to 14;
$R^1$ is $haloC_{1-10}alkyl$, $C_{1-10}alkyl$, $C_{2-10}alkenyl$, $C_{2-10}cycloalkyl$, $carboxyC_{1-10}alkyl$, $C_{1-10}alkoxycarbonylC_{1-10}alkyl$, aryl (such as phenyl), $aryl(C_{1-10})alkyl$ (such as phenyl $(C_{1-10})alkyl$) or $di(C_{1-6}alkyl)amino$;
and $R^2$ is a halo group; the process comprising halogenation of a compound of formula (III)

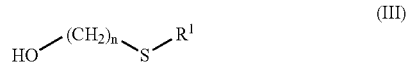

where n and $R^1$ are as defined above.
Novel compounds are also described and claimed.

12 Claims, 3 Drawing Sheets

OTHER PUBLICATIONS

Wakeling, A.E., et al., "Biology and Mode of Action of Pure Antioestrogens," J. Steroid Biochem., 30(1-6), 141-147 (1988).

Howell, A., et al., "Response to a specific antioestrogen (ICI 182780) in tamoxifen-resistant breast cancer," The Lancet, 345, 29-30 (1995).

Bowler, J., et al., "Novel Steroidal Pure Antiestrogens," J. Steroids, 71-99 (1989).

Kirschner, F.K., et al., "Quaternary Ammonium Alkyl Sulfide and Sulfoxide Cholinergic Agents," J. Amer. Chem. Soc., 77, 4599-4601 (1955).

Clinton, R.O., et al., "The Synthesis of Some Sulfur-Containing Amines," J. Amer. Chem. Soc., 67, 594-597 (1945).

Truce, W.E., et al., "Cyclopropyl Sulfones," J. Org. Chem., 26, 1463-1467 (1961).

Bennett, G.M., et al., "CCXXVI.—Derivaties of the Aliphatic Glycols. Part III." J. Chem. Soc. 1697-1701 (1931).

Bennett, G.M., et al., "The Formation of Large Ring Monosulphides from Halogenated Sulphides with Extended Carbon Chains," J. Chem. Soc., 1891-1897 (1938).

Iglesia, L. E., et al., "Simple Procedures for the Preparation of a.w-Hydroxyalkanethiols," Org. Prep. Proc. Int., 28(3), 319-324 (1996).

Shepard, K.L., et al., "Topically Active Carbonic Anhydrase Inhibitors. 4. [(Hydroxyalky)sulfonyl]benzene and [(Hydroxyalkyl)sulfonyl]thiophenesulfonamides," J. Med. Chem. 34, 3098-3105 (1991).

Oberkane, O., et al., "Synthesis of Polysulfides, Sulfoxides and Sulfones Containing Reactive Groups," Phosphorus, Sulfur and Silicon, 79, 245-256 (1993).

Masquelin, T., et al., "A Novel Solution- and Solid-Phase Approach to 2,4,5-Tri- and 2,4,5,6-Tetra- substituted Pyrimidines and Their Conversion into Condensed Heterocycles," Helvetica Chimica Acta, 81, 646-660 (1998).

Eliel, E.L., et al., "Endocyclic vs. Exocyclic Attack in Nucleophilic Displacement Reactions on Five- and Six-Membered Cyclic Onium Salts," J. Org. Chem., 41(6), 1052-1057 (1976).

Cagniant, P., et al., "A new heterocyclic sulfur compound, homothiachroman," C.R. Hebd. Seances Acad. Sciences, 223, 677-681 (1946).

Cagniant, P., et al., Condensed sulfur heterocycles. XI. Investigation of the semiaromatic bicyclic sulfur compounds: isothiochroman, homoisothiochroman, 4,5-benzo-1-thiacycloheptane, and 5,6-benzothiocane, Bull. Soc. Chim, 1998-2010 (1959).

* cited by examiner

FIG 1 Scheme 1 Prior art process

FIG 2  Scheme 2  Prior art process

PREPARATION PROCESS OF SOME HALOGENO-SUBSTITUTED MONOSULFIDES AND THEIR HYDROXY-MONOSULFIDE OR ISOTHIOURONIUM BROMIDE EQUIVALENTS AS INTERMEDIATES

This application is a national stage filing under 35 U.S.C. 371 of International Application No. PCT/GB02/04478, filed Oct. 3, 2002, which claims priority from United Kingdom Patent Application No. 0123961.5, filed Oct. 5, 2001, the specifications of which are incorporated by reference herein. International Application No. PCT/GB02/04478 was published under PCT Article 21(2) in English.

The invention relates to new processes useful in the preparation of intermediates to pharmaceutical compounds such as fulvestrant, and to novel intermediates for use in the process.

U.S. Pat. No. 4,659,516 describes a group of steroid derivatives, which have antioestrogenic activity.

Fulvestrant (Faslodex™, ZD9238, ICI 182,780) (Wakeling A E. J. Steroid Biochemistry 1990c; 37: 771-5, Wakeling A E, et al. J. Endocrinology 1987; 112: R7-10 and Wakeling A E et al. J. Steroid Biochemistry 1988; 3: 141-7) is a particular example of such a steroidal derivative and is the first in a new class of potent pure antioestrogens which is completely free of the partial agonist, oestrogen-like activity, associated with currently available antioestrogens like tamoxifen.

Fulvestrant has already demonstrated efficacy in a phase II trial in women whose breast cancer has progressed following tamoxifen therapy (Howell et al., The Lancet, 1995, 345. 29-30). Fulvestrant has a novel mechanism of action, described as an estrogen receptor downregulator, with clear evidence of anti-tumour activity in advanced breast cancer.

The chemical name for fulvestrant is 7-alpha-[9-(4,4,5,5,5-pentafluoropentylsulphinyl)nonyl]-estra-1,3,5(10)-triene-3,17β-diol, and this is represented as formula (I)

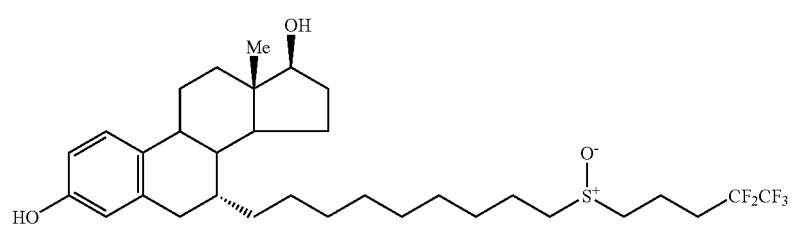

(I)

Figure 1:
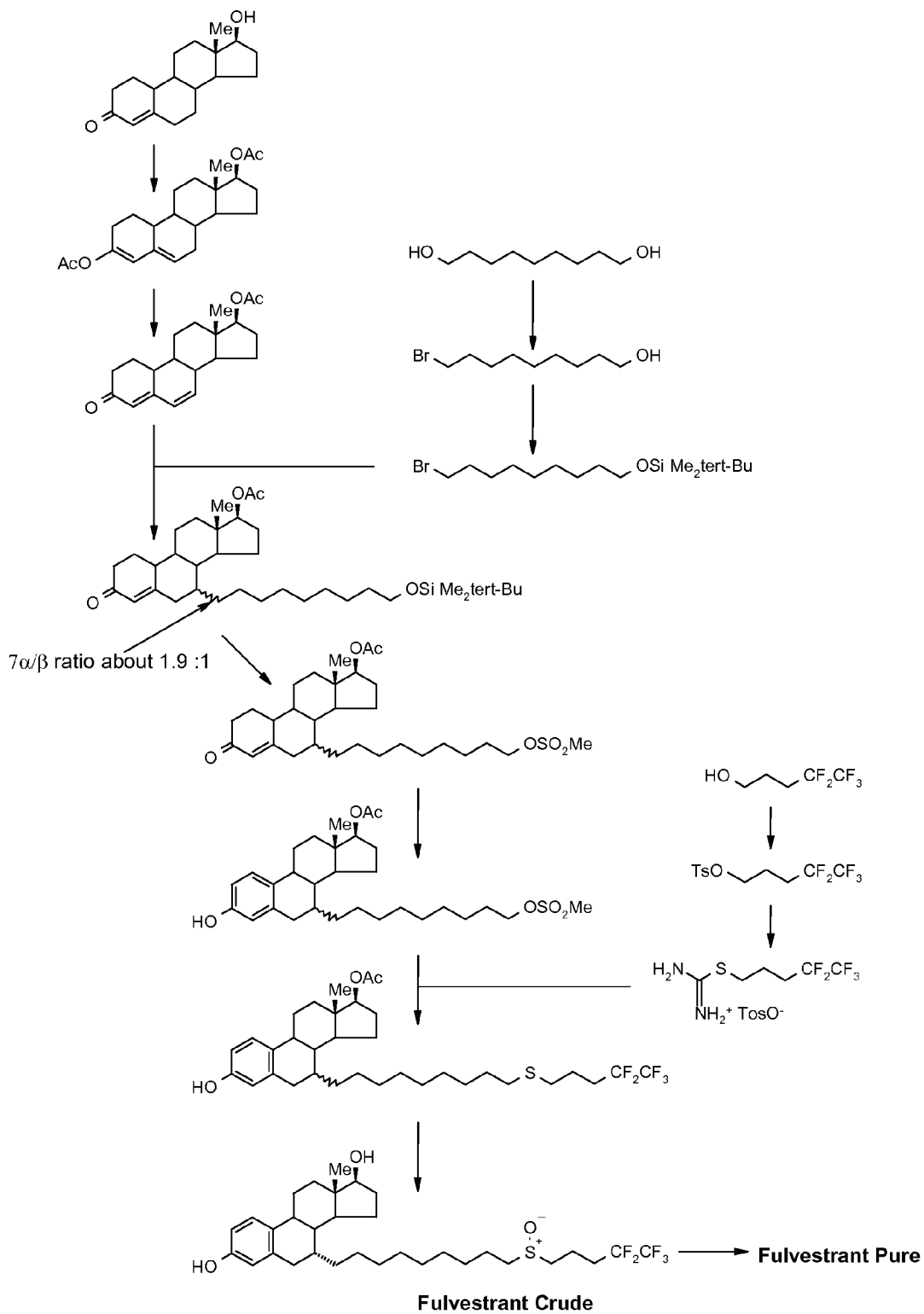
FIG. 1 shows schematically the prior art general process route of U.S. Pat. No. 4,659,516 as it would apply to the preparation of fulvestrant.

In U.S. Pat. No. 4,659,516, column 4 et seq., a general process route is described for the preparation of compounds of a similar type to fulvestrant. A summary of the general process as it would apply to the preparation of fulvestrant is described in FIG. 1. A process route is also described in Bowler J. (co-inventor of U.S. Pat. No. 4,659,516) Steroids (1989) 71-99 which is a similar route to that shown FIG. 1 hereinafter.

Figure 2:
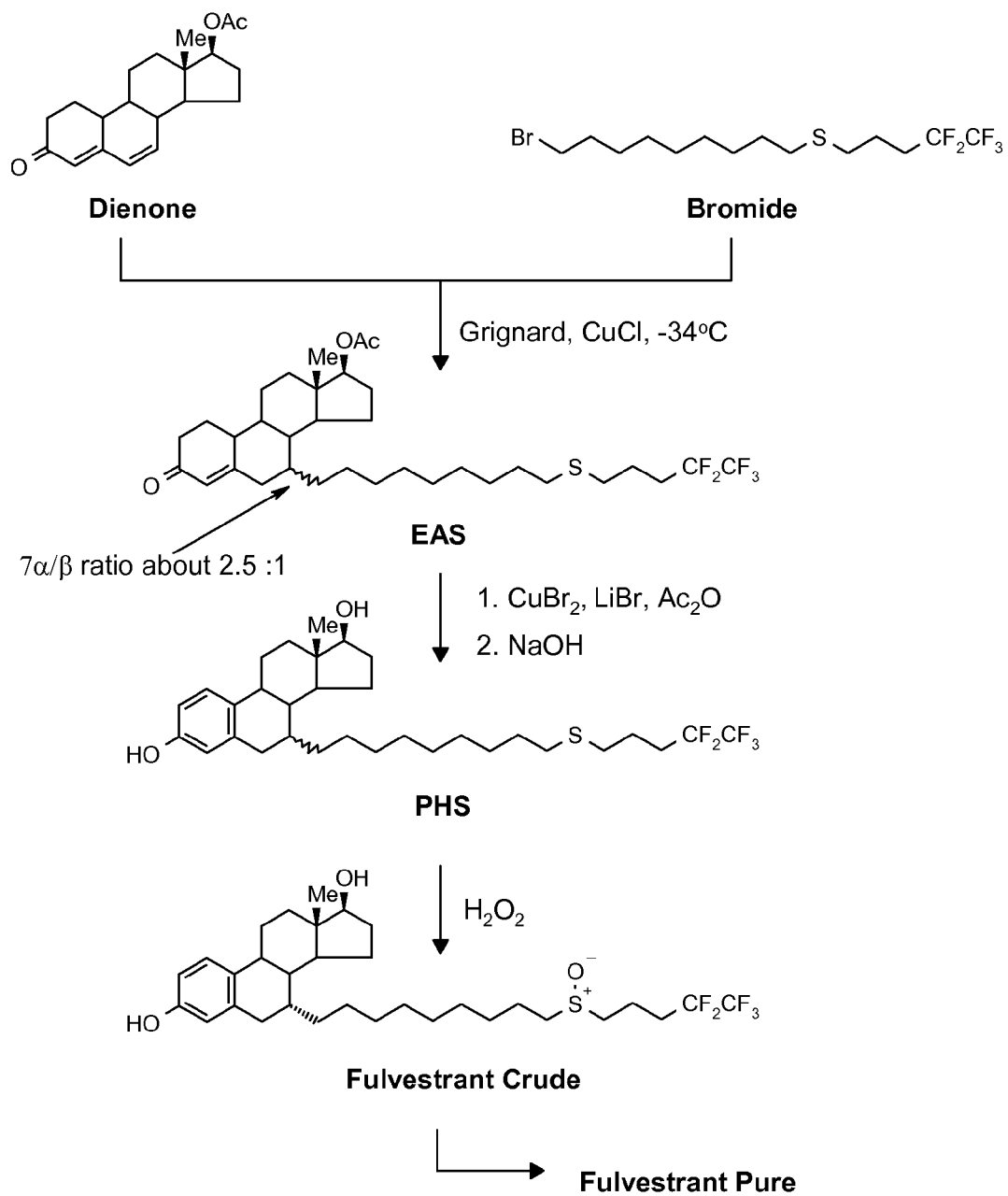
FIG. 2 shows schematically another route to fulvestrant as described in copending British patent application No. 0025211.3.

The applicants have found an improved route to this compound which is the subject of copending British Patent Application No. 0025211.3 and which is summarised in FIG. 2 herein after. A starting material used in this process is 9-bromononyl-4,4,5,5,5-pentafluoropentyl sulphide. This material is known for example from WO93/06124, where its preparation is described in Example 4 on page 11. The route used to prepare the compound in this case involved the coupling of 9-bromononanol to 4,4,5,5,5-pentafluoropentylmercaptan.

The applicants have found in particular, improved routes to these compounds.

According to the present invention there is provided a process for preparing an intermediate compound of formula (II)

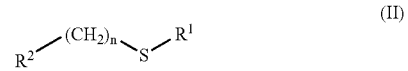

(II)

where n is an integer of from 3 to 14;

$R^1$ is haloC$_{1-10}$alkyl, C$_{1-10}$alkyl, C$_{2-10}$alkenyl, C$_{2-10}$cycloalkyl, carboxyC$_{1-10}$alkyl, C$_{1-10}$alkoxycarbonylC$_{1-10}$alkyl, aryl (such as phenyl), aryl(C$_{1-10}$)alkyl (such as phenyl (C$_{1-10}$)alkyl) or di(C$_{1-6}$alkyl)amino;

and $R^2$ is a halo group; the process comprising halogenation of a compound of formula (III)

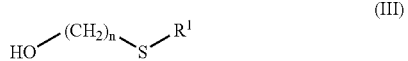

(III)

where n and $R^1$ are as defined above.

Suitably $R^2$ is bromo, chloro, fluoro or iodo, but is preferably bromo. Thus the halogenation is a bromination reaction. This is suitably effected using a halogenating agent, and particularly a brominating agent, in an organic solvent such as acetonitrile at moderate temperatures of from 0-40° C. and preferably at about 20° C. Organic solvents such as acetonitrile used in the halogenation reaction should preferably be dry (<0.1% w/w water), to prevent decomposition of the halogenating agent.

A particularly suitable brominating agent for use in the reaction is dibromotriphenylphosphorane, which is suitably prepared by adding bromine to triphenylphosphine in an organic solvent, preferably the same solvent as that used in the bromination reaction. Thus a particular example of a solvent is acetonitrile. Preferably equimolar amounts of triphenylphosphine and bromine are used.

Any excess brominating agent remaining after the halogenation reaction is suitably consumed by water during the work up to afford triphenylphosphine oxide and hydrogen bromide. In particular, this is effected by adding water to the reaction mixture and a significant excess of a weak base such as triethylamine. Preferably at least 1.5 equivalents of base are added, to ensure that both HBr produced as a by product of the bromination and also HBr resulting from decomposition of any excess brominating agent is neutralised. Once this has been achieved, the mixture may be concentrated by distillation, preferably under reduced pressure to ensure that the temperature does not result in decomposition of the desired product. In the case of Fulvestrant bromide, this is suitably below 40° C.

Product is suitably extracted from this work-up mixture by extraction into a low boiling point solvent such as isohexane. Extraction is suitably effected at temperatures in excess of 20° C. in order to prevent any triphenylphosphine crystallising out. However suitably the temperature is kept below 40° C. to prevent decomposition of Fulvestrant bromide in particular. After washing with for example acetonitrile and/or aqueous acetonitrile, solvent may then be removed from the product by concentration, for example using distillation under reduced pressure, so as to ensure that the maximum batch temperature does not exceed 60° C.

Compounds of formula (II) obtained using this method may be subject to further purification using conventional methods before being used as a starting material for the preparation of compounds such as fulvestrant. Suitable methods include distillation, in particular distillation under reduced pressure, for instance using a wiped film evaporator.

Thus particular examples of compounds of formula (III) are those where $R^1$ is haloC$_{1-10}$alkyl, and in particular is a group of formula —(CH$_2$)$_3$CF$_2$CF$_3$. Such compounds are thus of formula (IIIA)

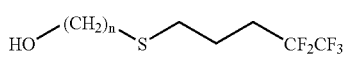

(IIIA)

where n is as defined above, and in particular is 9.

A further particular group of compounds of formula (III) are compounds of formula (IIIB)

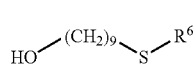

(IIIB)

where $R^6$ is haloC$_{1-10}$alkyl.

Compounds of formula (IIIA) and (IIIB) are novel and therefore form a further aspect of the invention. Compounds of formula (III) including (IIIA) and (IIIB) may be prepared by conventional methods. Suitably they are prepared by reacting a compound of formula (IV)

(IV)

where n is as defined in relation to formula (II) and M$^+$ is a metal ion, in particular an alkali metal ion such as sodium or potassium and preferably sodium, with a compound of formula (V)

$$Z\text{-}R^1 \quad (V)$$

where $R^1$ is as defined above in relation to formula (II) and Z is a leaving group.

Suitable leaving groups Z are conventional groups such as halo, mesylate and tosylate, but in a particularly preferred embodiment, Z is a mesylate group.

The reaction is suitably effected at elevated temperature for example of from 30 to 75° C., and preferably at the reflux temperature of the solvent, in the presence of a strong base such as alkali metal hydroxide, for example sodium hydroxide. Suitably an excess of the compound of formula (V) is included in the reaction mixture to ensure that all the compound of formula (IV) is consumed in the reaction.

Compounds of formula (III) are suitably recovered from the reaction mixture following a work-up procedure involving washes, in particular using water, and distillation to remove remaining organic solvent.

Compounds of formula (IV) are suitably prepared in situ by reacting a compound of formula (VI)

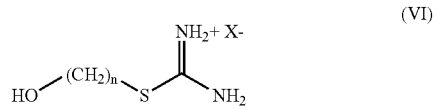

(VI)

where n is as defined above in relation to formula (II), and X is a halide ion, in particular bromine, with a base. Suitably the reaction is effected in an aqueous solvent. Particular bases for use in the reaction are strong bases such as alkali metal hydroxides, in particular sodium hydroxide. The base is suitably present in a considerable excess, for example 6 equivalents. Elevated temperatures for example from 40-75° C. are suitably employed.

Compound of formula (V) are suitably prepared when required for use, for example by reacting a compound of formula (VII)

$$HO\text{—}R^1 \quad (VII)$$

where $R^1$ is as defined above, with a compound of formula (VIII)

$$Z\text{-}R^7 \quad (VIII)$$

where Z is as defined in relation to formula (V) and $R^7$ is halide such as chloride. The reaction is suitably effected in the presence of a weak base such as triethylamine. Particular examples of compounds of formula (VIII) are mesyl halides such as mesyl chloride In this case, the reaction is suitably effected in the substantial or complete absence of water, and alcohols, which would hydrolyse the mesyl halide. Preferably a slight excess of mesyl halide is incorporated into the reaction mixture. Moderate temperatures for example of from 0-30° C. and conveniently at about 20° C. are employed.

Compounds of formula (VI) where X is bromine are novel compounds and form a further aspect of the invention.

Compounds of formula (VI) are suitably prepared by reacting a compound of formula (IX)

(IX)

where $R^5$ is halo such as chloro, bromo, fluoro or iodo and preferably bromo, with thiourea. The reaction is suitably effected in an organic solvent such as toluene, and/or an alcohol such as isopropanol. Elevated temperatures, for example from 50-100° C. and conveniently the reflux temperature of the solvent, are employed. Suitably, just less that one equivalent of thiourea is added to the reaction mixture to ensure that not remains in the product, as this may give rise to unwanted intermediates later in the process.

Compounds of formula (VI) are suitably extracted from the reaction mixture by filtration. The product may then be dried, although in some cases, complete drying may not be desirable as certain of these products may have a tendency to be dusty solids. It may be easier to handle these as damp pastes on the plant (or production) scale.

Compounds of formula (IX) are known compounds and may be prepared by conventional routes. The applicants have found however that, where $R^5$ is a preferred bromo group, it is suitably prepared by reacting the corresponding diol of formula (X)

(X)

with hydrogen bromide. In order to ensure efficient production of the desired monobromo product of formula (IX), the amount of hydrogen bromide is suitably present in at least 3.0 mole equivalents to ensure complete reaction of the diol. Furthermore, the reaction is suitably effected in the presence of an organic solvent such as toluene, in which the desired monobromoalcohol is soluble. This results in partitioning of the desired product into the organic phase and so prevents formation of a significant quantity of the over-bromination product.

In particular in the above compounds (II), (III), (V), (V) and (VII), $R^1$ is a haloalkyl group and in particular is a group of formula —$(CH_2)_3CF_2CF_3$.

Suitable examples of n are integers of from 6 to 12 and particularly 9.

Figure 3:
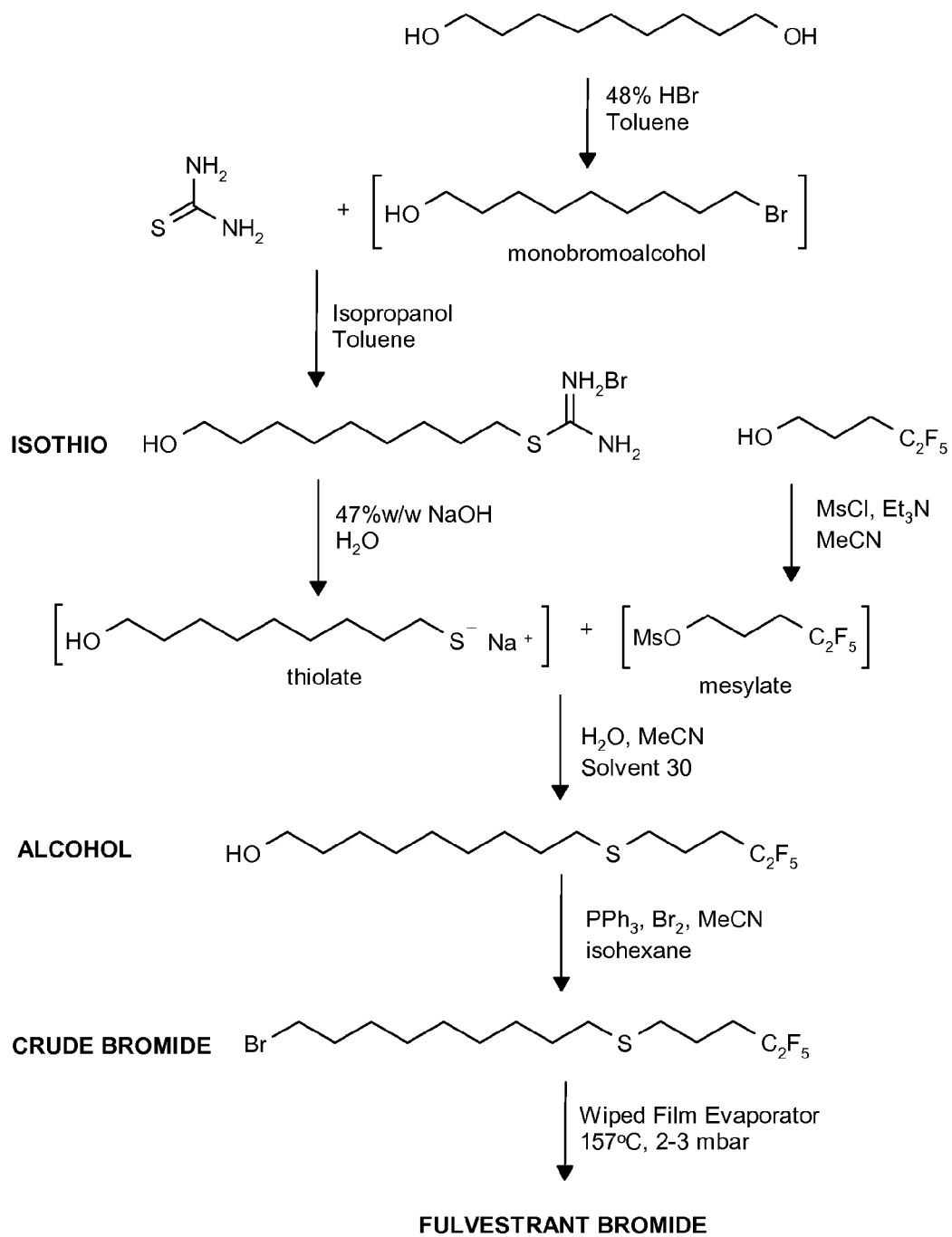
FIG. 3 shows schematically the route to the preparation of fulvestrant according to the present invention.

The invention is illustrated by the following non-limiting example, which is summarised in FIG. 3 hereinafter.

EXAMPLE 1

Preparation of Fulvestrant Isothio
(See FIG. 3) Step 1

1,9-Nonanediol (1.0 mol eq) was converted to 9-bromononylalcohol (0.95 mol eq) by treatment with 48% hydrobromic acid (3.0 mol eq) in toluene (11.8 rel vol). The reactants were heated to reflux (93° C.) for 7 hours to complete the reaction, then cooled to 75° C. The aqueous phase was separated and the toluene solution washed with water (0.89 rel vol) at 75° C. The organic phase was then concentrated by distillation (to 4.75 rel vol) and further toluene added (1.14 rel vol).

The solution of 9-bromononylalcohol in toluene was added to a solution of thiourea (0.95 mol eq) in isopropanol (2.52 rel vol) at 70° C. The reactants were heated to reflux (~84° C.) for 20 hours to complete formation of the isothiouronium bromide. The mixture was cooled to 0 to −5° C., then the product was isolated by filtration and washed with solvent 30 (2.0 rel vol). {Solvent 30 is a non-aromatic hydrocarbon solvent, with a boiling point of about 120° C., available from Multisol Limited, Cheshire, UK). The product was dried with cold nitrogen to a paste strength of about 95%. The yield of Fulvestrant Isothio is typically 90%.

Preparation of Fulvestrant Alcohol

Step 2

A solution of mesyl chloride (1.25 mol eq) in acetonitrile (1.5 rel vol) was added to pentafluoropentanol (1.10 mol eq) and triethylamine (1.40 mol eq) in acetonitrile (2.0 rel vol) at 20° C. The mixture was held for 30 minutes to complete the mesylation. A solution of Isothio (1.0 mol eq) in water (3.0 rel vol) was added at 40° C. followed by 47% w/w caustic liquor (6.0 mol eq). The mixture was heated to reflux (75° C.) for 8 hours to complete the reaction. The lower layer was separated at 40° C.

Solvent 30 (5.0 rel vol) was added and the organic extract washed with water (1.0 rel vol) and then with aqueous hydrochloric acid (1.25 mol eq) and water (1.0 rel vol) (all separations at 40° C.). The Solvent 30 solution was heated and a small amount of distillate collected (600 mbar, to batch temperature 85° C.). The mixture was cooled to 10° C. to crystallise the product, which is isolated by filtration and washed with solvent 30 (2.0 rel vol). Fulvestrant Alcohol (mp 40-42° C.) was dried at 25° C. The yield of Fulvestrant Bromide is typically about 80%.

Step 3

Preparation of Fulvestrant Bromide

Dibromotriphenylphosphorane was prepared by adding bromine (1.25 mol eq) to a slurry of triphenylphosphine (1.25 mol eq) in dry acetonitrile (2.25 rel vol) at 20° C. The mixture was stirred for 1 hour to complete the reaction. A solution of alcohol from step 2 (1.0 mol eq) in acetonitrile (2.5 rel vol) was prepared at 35° C., then added to the brominating agent at 20° C. The mixture was held at 20° C. for 1 hour to complete the reaction. Triethylamine (1.6 mol eq) and water (1.0 rel vol) were added and the mixture concentrated by distillation (200 mbar). The product was extracted into isohexane (4.0 rel vol) at 30° C., washed twice with aqueous acetonitrile (2×2 rel vol of 1:1 MeCN: water) and once with acetonitrile (0.5 rel vol) at 30° C. Removal of the solvent by vacuum distillation (with a batch temperature not exceeding 60° C.) gives the product as an oil. The yield of Fulvestrant Bromide is typically about 85%.

The invention claimed is:

1. A process for preparing a compound of formula (II)

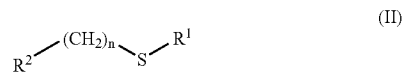
(II)

where n is an integer of from 3 to 14;
$R^1$ is halo$C_{1-10}$alkyl and $R^2$ is a halo group;
the process comprising halogenation of a compound of formula (III)

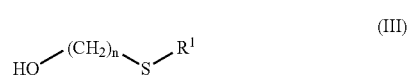
(III)

where n and $R^1$ are as defined above.

2. A process according to claim 1, where $R^2$ is bromo.

3. A process of claim 1 which comprises preparing a compound of formula (III)

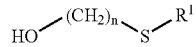
(III)

where n is an integer of from 3 to 14;
$R^1$ is haloC$_{1-10}$alkyl;
by reacting a compound of formula (IV)

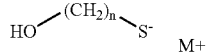
(IV)

where n is an integer of from 3 to 14 and $M^+$ is a metal ion, with a compound of formula (V)

Z-R$^1$ (V)

where $R^1$ is haloC$_{1-10}$alkyl and Z is a leaving group.

4. A process according to claim 3, wherein Z is a mesylate group.

5. A process according to claim 3, where the compound of formula (IV) is prepared by reacting a compound of formula (VI)

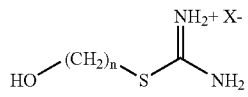
(VI)

where n is an integer of from 3 to 14, and X is a halo group, with a base.

6. A process according to any one of claims 1 to 4, wherein $R^1$ is a group of formula —(CH$_2$)$_3$CF$_2$CF$_3$.

7. A process according to any one of claims 1 to 4, wherein n is 9.

8. A compound of formula (IIIA)

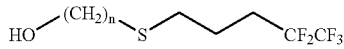
(IIIA)

where n is 9.

9. A compound of formula (IIIB)

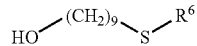
(IIIB)

where $R^6$ is haloC$_{1-10}$alkyl.

10. A compound of formula (IV)

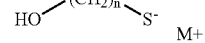
(IV)

where n is 9 and $M^+$ is an alkali metal ion selected from sodium or potassium.

11. A compound of formula

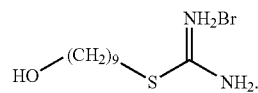

12. A process for preparing a compound of formula (VI)

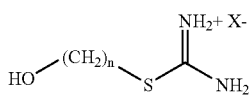
(VI)

where n is 9 and X is a halo group, which process comprises reacting isothiourea with a compound of formula (IX)

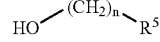
(IX)

where $R^5$ is halo.

* * * * *